United States Patent [19]

Mike

[11] 4,226,829

[45] Oct. 7, 1980

[54] RENEWABLE VAPORIZER FOR AIR TREATMENT AND THE LIKE

[76] Inventor: Andrew Mike, 141 Deauville Ct., Fort Mitchell, Ky. 41017

[21] Appl. No.: 948,548

[22] Filed: Oct. 4, 1978

[51] Int. Cl.$^3$ .................. A01M 1/20; A61L 9/01; A61L 9/12

[52] U.S. Cl. .................. 422/123; 422/305; 422/306; 261/DIG. 17; 261/DIG. 65; 239/54; 239/55; 43/129; D23/150

[58] Field of Search .................. 422/4, 5, 305, 306, 422/123; 424/76; 239/6, 54, 55, 60; 119/160; 261/DIG. 65, DIG. 17; 128/187; 43/129; D23/148, 150

[56] References Cited

U.S. PATENT DOCUMENTS

| | | | |
|---|---|---|---|
| D. 162,679 | 3/1951 | Munnecke | D23/150 |
| D. 193,966 | 10/1962 | D'Alesandro | D23/148 |
| 274,425 | 3/1883 | Wells | 239/55 |
| 361,599 | 4/1887 | Spinner | 128/187 |
| 1,954,893 | 4/1934 | Saeks | 422/5 |
| 2,586,761 | 2/1952 | Eskola | 239/60 |
| 2,603,532 | 7/1952 | Wheeler et al. | 422/5 |
| 3,558,055 | 1/1971 | Storcheim | 239/55 |
| 3,790,081 | 2/1974 | Thornton et al. | 239/55 |
| 4,146,566 | 3/1979 | Gaiser | 422/306 |
| 4,157,787 | 6/1979 | Schwartz | 239/60 |

Primary Examiner—Bradley R. Garris
Attorney, Agent, or Firm—Frost & Jacobs

[57] ABSTRACT

A vaporizer for air treatment and the like producing vapors which can be renewed to provide effective operation for an extended period of time. The vaporizer comprises an hourglass-shaped container having a pair of adjacent chambers communicating by means of a restrictive orifice. Each chamber has an opening in the end covered by a porous membrane. The container contains a supply of particulate fluid-like carrier material carrying a volatile vapor-producing treating material. A part of the treating agent is transferred by the carrier material to the membrane for producing air treating vapors by volatilization or evaporation of the treating agent. Inversion of the container, mixes and redistributes the treating agent among the carrier vehicle particles and exposes a freshly loaded vapor producing membrane.

14 Claims, 2 Drawing Figures

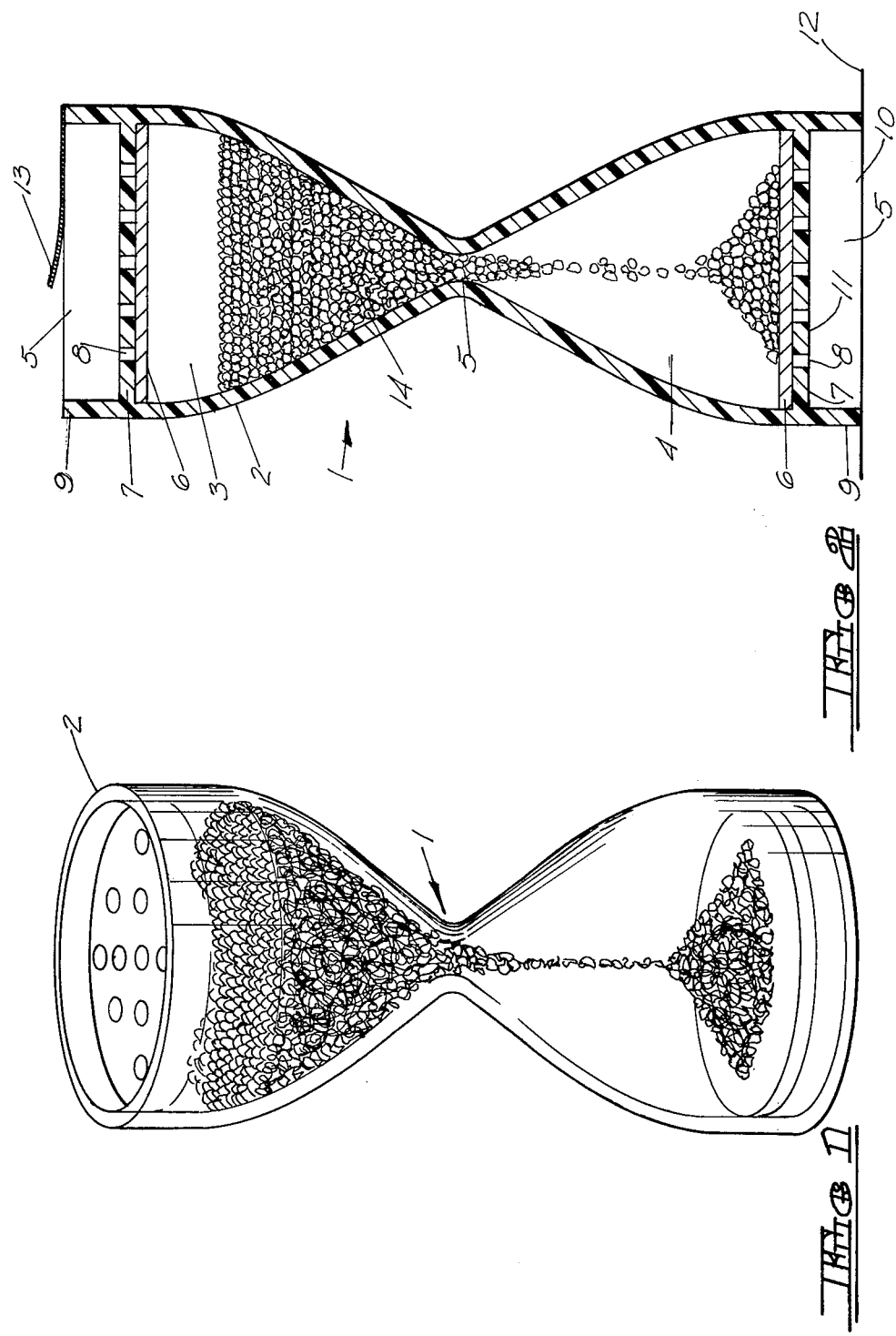

RENEWABLE VAPORIZER FOR AIR TREATMENT AND THE LIKE

BRIEF SUMMARY OF THE INVENTION

The present invention relates generally to vaporizers of the type utilizing a volatile fluid for treating air and the like, and more particularly to a vaporizer of this type producing vapors which can be renewed to provide effective operation for an extended period of time.

Deodorizers, fumigators, purifiers, and other types of vaporizer-type air treatment devices using a volatile fluid are well known in the art to produce vapors in particular ways to remove odors, discourage pests, etc. Some of these devices rely on solid or solid-like treatment agents which sublime or evaporate upon exposure to air. Other treatment devices utilize evaporation of liquids either directly, through sprays, drip dispensers or the like, or indirectly through wicks or saturated pads, to provide air treating vapors.

The present invention utilizes a container having a supply of fluid-like carrier material carrying a volatile vapor-producing treatment material. The container has at least one opening covered by a porous membrane so that when the fluid-like carrier material comes in contact with the membrane, a part of the treating agent is transferred to the membrane. A part of the transferred treating agent is adsorbed or absorbed by the membrane and is brought into contact with the outer surface where the necessary air treating vapors are produced by volatilization or evaporation of the treating agent.

The vapor producing treating agent can be absorbed by an absorptive carrier material or vehicle, or may be contained on the surface of the carrier vehicle in the case of a non-absorptive carrier.

In a preferred embodiment, the container is formed in the shape of an hourglass with an opening on either end covered by a porous membrane, and a central restrictive orifice positioned between the adjacent chambers of the container. In this arrangement, when the container is inverted, the carrier vehicle particles will sift downwardly through the restrictive orifice to mix and randomize the particles, thereby redistributing the treating agent which is then transferred to the porous membrane at the lower end of the container. The porous membrane at the upper end of the container will continue to produce air treating vapors until the supply of treating agent transferred to the membrane has been exhausted.

In another embodiment, a flange is provided at each end of the container so that the porous membrane does not rest directly on the supporting surface such as a table or the like, thereby producing a trapped air space between the upper surface of the support and the porous membrane. This arrangement produces an immediate "bloom" of treating agent when the container is inverted.

As will become more apparent in the detailed description which follows, the vaporizing action of the vaporizer of the present invention may be easily renewed by merely changing the orientation of the container. When all of the treating agent contained on the carrier material has been expended, the container may be discarded or additional treating agent added to the carrier vehicle material. In addition, a colored or otherwise visually attractive treating agent or carrier vehicle may be used with a transparent or translucent container to provide a decorative as well as useful air treating vaporizer.

BRIEF DESCRIPTION OF THE DRAWINGS

FIG. 1 is a perspective view of the renewable vaporizer of the present invention.

FIG. 2 is a cross sectional view of the renewable vaporizer of the present invention.

DETAILED DESCRIPTION

In the preferred embodiment shown in FIG. 1 and FIG. 2, the renewable vaporizer, shown generally at 1, comprises a thin-walled hourglass-shaped container 2 containing an upper frusto-conical shaped chamber 3 communicating with a similarly shaped lower chamber 4 by means of a restricted opening or orifice 5a. Container 2 may be constructed of any suitable material such as metal, paper, plastic, glass or the like. In a preferred embodiment, container 2 is constructed of a translucent or transparent material so that the contents of the vaporizer 1 may be easily observed as will be explained in more detail hereinafter. The ends of chambers 3 and 4 are open as at 5 and are covered with a porous membrane 6 extending completely across opening 5. Membrane 6 may be constructed of any suitable porous material and may be woven or non-woven, absorptive or adsorbive, hydrophilic, inert or hydrophobic. Suitable materials for membrane 6 include man-made fibers such as nylon, cellulose, or rayon, which may be coated or uncoated to modify their absorptive properties, as well as natural fibers such as cotton, paper or paper products. As will be described in more detail hereinafter, the treating agent carried on the carrier vehicle is transferred to the membrane and remains thereon either as a vapor or liquid on the surface of the membrane, or within or between the fibers thereof. It will be understood that porous membrane 6 may be constructed of a foraminous material or a solid sheet containing a plurality of small openings permitting the treating agent vapor or liquid to pass from chamber 3 or 4 to the outermost surface of membrane 6.

It also will be understood that the openings in membrane 6 must be large enough to permit the passage of treating vapors or liquids, but small enough to prevent the carrier vehicle from being discharged from the container. To provide additional strength and rigidity to the structure in the case of a thin fragile membrane 6, a perforated support plate 7 containing numerous spaced apertures extending therethrough, one of which is shown at 8, is provided adjacent the outermost surface of membrane 6. Apertures 8 permit the passage of treating fluid while protecting membrane 6 against inadvertent ruptures.

In a preferred embodiment, each end of vaporizer 1 is provided with a thin-walled upstanding circular flange 9 which is of such a height as to provide a suitable trapped air space 10 between the outermost surface 11 of perforated support plate 7 and the supporting surface 12 of a table or the like upon which vaporizer 1 is placed. As will be explained in more detail hereinafter, this trapped air space and the accompanying vapors generated therein provide an initial "bloom" when vaporizer 1 is initially lifted from support surface 12 to provide immediate air treatment as well as a signal that the treating agent is available and the vaporizer is operational. In applications where this feature is not desired, flange 9 may be eliminated such that support plate 7 rests directly on the support surface 12.

Each end of vaporizer 1 may be provided with a removable impervious material such as that shown partially removed at 13 in FIG. 2 which retains the volatile treating agent within the vaporizer until it is ready for use. At that time, impervious material 13 may be removed from one or both ends of container 1 to provide air treatment.

Container 1 is also partially filled with a particulate carrier vehicle or material 14 so dimensioned as to easily flow through restricted orifice 5a. Carrier vehicle 14 may comprise absorptive particles such as talc, alumina, or clay, or cellulosic material such as starch, sugar, inorganic salts or the like. The use of such materials permits the treating agent to be described hereinafter to be absorbed and carried by the particles. Alternatively, the treating agent may be carried on the surfaces of non-absorptive particles such as beads constructed of glass, plastic or other inert materials. The particles comprising vehicle 14 may be smooth or irregularly shaped and of any desired size which will not unnecessarily interfere with their passage between chambers 3 and 4. In addition, the particles may be colored or otherwise visually attractive to provide a decorative as well as useful air treating vaporizer.

The particular treating agent used will depend upon the air treatment required. Exemplary types of volatile treating agents include liquids in the form of perfumes, insecticides, pesticides, air fresheners, etc. Alternatively, the carrier vehicle itself may be the treatment agent in the form of a solid or semi-solid so that contact between the carrier vehicle and membranes 6 will serve to transfer the desired amount of treating agent to the membrane. It will be understood that the viscosity of the treating agent as well as the degree of wetting of the carrier vehicle 14 will in part determine the flow characteristics of the carrier vehicle through restrictive orifice 5a.

In operation, container 2 is initially oriented so that the carrier vehicle 14 is in contact with one or the other of membranes 6. A sufficient amount of time is then permitted to elapse to permit the treating agent to be transferred from the carrier vehicle to the adjacent membrane. The container is then inverted, and the protective covering 13 removed. A part of the treating agent transferred to the membrane 6 will then be released as a vapor by volatilzation of the treating agent on the outer surface of membrane 6.

When container 2 has been inverted, the carrier vehicle will immediately begin to sift downwardly through restrictive orifice 5a into lower chamber 4. As the carrier vehicle passes through the restrictive orifice, it is randomly mixed to redistribute the treating agent over the entire surface of the carrier vehicle particles. As the carrier vehicle continues to sift downwardly, it is spread substantially evenly over the innermost surface of lower membrane 6 to transfer a part of the treating agent to the membrane.

When vapors are no longer being emitted by the upper membrane, container 2 can be again inverted so that an unexposed membrane is brought into contact with the air and a new quantity of vapors released. The vapors initially generated by the lower membrane and trapped within the enclosed air space 10 will be immediately released as a "bloom" of vapor to provide immediate air treatment as well as an indication that the vaporizer is working.

In the preferred embodiment where container 2 is constructed of a transparent or translucent material, the progress of the carrier vehicles between the adjoining chambers 3 and 4 can be observed. In the event that the particles become jammed in restrictive orifice 5a, the container can be slightly jarred to continue the downward flow of the carrier vehicle material.

When a sufficient amount of the treating agent contained on the carrier vehicle has been used so that the vaporizer no longer provides effective air treatment, the entire vaporizer may be discarded, or a quantity of appropriate treating agent may be added through either end of container 2 to thoroughly wet and recharge the carrier vehicle. Operation of the vaporizer may then continue as described hereinabove.

It will be understood that various changes in the details, materials, steps and arrangements of parts, which have been hereindescribed and illustrated in order to explain the nature of the invention, may be made by those skilled in the art within the principle and scope of the invention as expressed in the appended claims. For example, although for purposes of an exemplary showing container 2 has been described and illustrated in the shape of an hourglass, it will be understood that any shaped container containing the necessary treating agent and carrier vehicle, and having at least one opening covered by a porous membrane such as that described hereinabove may be utilized to provide the vaporizer of the type described. In the case of such a vaporizer lacking adjacent chambers and a restrictive orifice, randomization and mixing of the carrier vehicle, and transfer of the treating agent to the porous membrane may be accomplished by merely inverting or shaking the container. It will be further understood that suitable access may be provided to the container so that the carrier vehicle may be replaced with carrier vehicle having a full charge of treating agent.

The embodiments of the invention in which an exclusive property or privilege is claimed are as follows:

1. A renewable vaporizer for producing air treating vapors comprising a container having at least one opening therein, a supply of fluid-like carrier material carrying a vapor producing treating agent contained within said container; and a porous membrane covering said opening, said fluid-like material being in contact with said membrane to transfer a part of said treating agent thereto when said container is positioned in a first orientation, said membrane operating to bring a part at least of said transferred treating agent into contact with the outer surface of said membrane for producing air treating vapors.

2. The vaporizer according to claim 1 including a perforated plate-like support member extending across said container adjacent said membrane to support said membrane.

3. The vaporizer according to claim 1 wherein said container includes a flange-like lip extending outwardly adjacent said membrane for forming an air space adjacent said outer surface of said membrane.

4. The vaporizer according to claim 1 wherein said vaporizer includes a removable and imperforate sheet temporarily covering said membrane.

5. The vaporizer according to claim 1 wherein said container is at least partially optically transmissive.

6. The vaporizer according to claim 1 wherein said container comprises a pair of chambers interconnected by a restrictive orifice, each of said chambers having an opening disposed therein, each of said openings being covered with a said membrane, said fluid-like material being in contact with one of said membranes when said container is positioned in said first orientation, said fluid-like material being in contact with the other of said membranes when said container is in a second orientation, said fluid-like material passing through said restrictive orifice when said container is moved between said first and second orientations to mix said material and redistribute said treating agent.

7. The vaporizer according to claim 6 wherein said container is substantially hourglass-shaped.

8. The vaporizer according to claim 1 wherein said carrier material comprises a particulate material.

9. The vaporizer according to claim 8 wherein said particulate material absorbs said treating agent.

10. The vaporizer according to claim 8 wherein said particulate material is substantially non-absorptive, said treating agent being carried substantially on the surface of said particulate material.

11. The vaporizer according to claim 10 wherein said particulate material is comprised of inorganic beads.

12. The vaporizer according to claim 1 wherein said treating agent comprises a volatile fluid.

13. The vaporizer according to claim 1 wherein said membrane absorbs said treating agent.

14. The vaporizer according to claim 1 wherein said membrane is substantially non-absorptive.

* * * * *